(12) United States Patent
Muturi

(10) Patent No.: US 11,700,898 B2
(45) Date of Patent: Jul. 18, 2023

(54) CALF MUSCLE ENHANCEMENT PAD

(71) Applicant: Eve G. Muturi, Las Vegas, NV (US)

(72) Inventor: Eve G. Muturi, Las Vegas, NV (US)

(\*) Notice: Subject to any disclaimer, the term of this patent is extended or adjusted under 35 U.S.C. 154(b) by 0 days.

(21) Appl. No.: 17/238,625

(22) Filed: Apr. 23, 2021

(65) Prior Publication Data

US 2022/0061436 A1 Mar. 3, 2022

Related U.S. Application Data

(60) Provisional application No. 63/103,823, filed on Aug. 28, 2020.

(51) Int. Cl.
*A41D 27/26* (2006.01)
*A61F 2/60* (2006.01)
*A63B 71/12* (2006.01)
*A41B 11/14* (2006.01)
*A61F 2/50* (2006.01)

(52) U.S. Cl.
CPC ............... *A41D 27/26* (2013.01); *A61F 2/60* (2013.01); *A63B 71/1225* (2013.01); *A41B 11/14* (2013.01); *A41D 2400/38* (2013.01); *A61F 2002/5001* (2013.01)

(58) Field of Classification Search
CPC ........ A61F 2002/5001; A41D 2400/38; A41D 27/26
See application file for complete search history.

(56) References Cited

U.S. PATENT DOCUMENTS

2018/0185171 A1\* 7/2018 Sifuentes Lumbreras ................. A41B 11/02
2019/0059454 A1\* 2/2019 Bellissimo ......... A41D 13/0543

FOREIGN PATENT DOCUMENTS

DE 203 14 270 \* 9/2003

OTHER PUBLICATIONS

Screen capture from YouTube vide clip entitled "Silicone calf pads leg makers forskinny boy girs", 1 page, uploaded on Apr. 22, 2019. Retrieved from internet: <http://www.youtube.com/watch?v=HmPKZklnjby> (Year: 2019).\*
DE 201 14 270 Translation, Lipah, Sep. 2003.\*

\* cited by examiner

*Primary Examiner* — Bruce E Snow
(74) *Attorney, Agent, or Firm* — Jacob M. Ward; Ward Law Office LLC

(57) ABSTRACT

A calf muscle enhancement pad; the calf muscle enhancement pad includes a pad with a body having a concave first-side and a second-side opposing the first-side. The first-side includes an adhesive layer for removably securing the pad to a calf portion of a leg of a user-wearer. The adhesive layer may include a pressure-sensitive adhesive. The pad further includes a removable cover for concealing the adhesive layer before use. The second-side includes a calf-muscle-like extension having a profile of a sculpted calf muscle for enhancing a natural appearance of the calf portion and overall leg of the user-wearer during wear.

2 Claims, 6 Drawing Sheets

CALF MUSCLE ENHANCEMENT PAD

CROSS-REFERENCE TO RELATED APPLICATION(S)

The present application is related to and claims priority to U.S. Provisional Patent Application No. 63/103,823 filed Aug. 28, 2020, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of enhancement legwear of existing art and more specifically relates to pads for enhancing legs.

RELATED ART

Sculpted calf muscles are desirous however to achieve strong and appealing calves a person must work out on a consistent and aggressive basis. This is time consuming, physically demanding and requires discipline.

Leggings, for example, are an article of clothing designed to fit snuggly around a wearer's leg thereby exposing the shape of the wearer's leg. A person wearing legging may desire to enhance the appearance of his or her lower legs. Similarly, a person wearing socks with an outfit that exposes the socks and hence the shape of the wearer's legs, may find it desirable to enhance the appearance of his or her lower legs. A suitable solution is desired.

U.S. Pat. No. 2015/0047102 to Beverly Pillow relates to enhancement legwear with removable pads. The described enhancement legwear with removable pads includes legwear having at least two interior pockets in the calf area and ankle area of the legwear for inserting pads to enhance the physical structure of a person's leg between the knee and the ankle.

SUMMARY OF THE INVENTION

In view of the foregoing disadvantages inherent in the known pads for enhancing legs art, the present disclosure provides a novel calf muscle enhancement pad. The general purpose of the present disclosure, which will be described subsequently in greater detail, is to provide a calf muscle enhancement pad.

A calf muscle enhancement pad is disclosed herein. The calf muscle enhancement pad includes a pad with a body having a concave first-side and a second-side opposing the first-side. The first-side includes an adhesive layer for removably securing the pad to a calf portion of a leg of a user-wearer. The adhesive layer may include a pressure-sensitive adhesive. The pad further includes a removable cover for concealing the adhesive layer before use. The second-side includes a calf-muscle-like extension comprising a profile of a sculpted calf muscle for enhancing a natural appearance of the calf portion of the leg of the user-wearer during wear.

A method of use is further disclosed. The method includes the steps of: providing a pad with a body having a concave first-side including an adhesive layer for removably securing the pad to a calf portion of a leg of a user-wearer and a second-side opposing the first-side and having a calf-muscle-like extension comprising a profile of a sculpted calf muscle for enhancing a natural appearance of the calf portion of the leg of the user-wearer during wear; step two, removing a removable cover and exposing the adhesive layer of the concave first-side of the pad; step three, securing the pad to the calf portion of the leg of the user-wearer; and step four, optionally removing the pad.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a calf muscle enhancement pad, constructed and operative according to the teachings of the present disclosure.

The various embodiments of the present invention will hereinafter be described in conjunction with the appended drawings, wherein like designations denote like elements.

DETAILED DESCRIPTION

Figure 1:
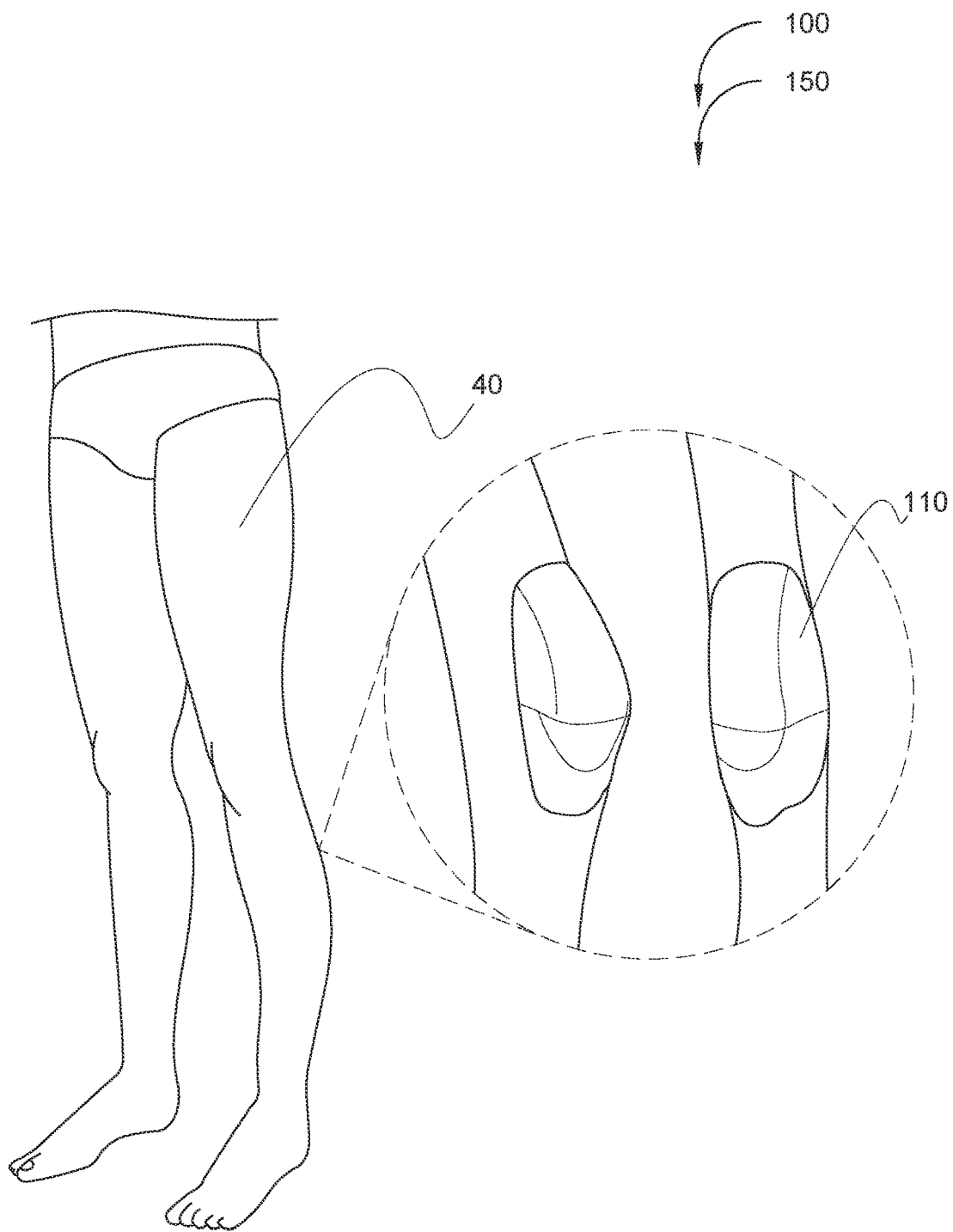
FIG. 1 is a perspective view of the calf muscle enhancement pad during an 'in-use' condition, according to an embodiment of the disclosure.

As discussed above, embodiments of the present disclosure relate to a pad for enhancing legs and more particularly to a calf muscle enhancement pad including a foam member molded to appear as a sculpted calf muscle as used to improve the appearance of a calf muscle and overall appearance of a leg.

Generally, the calf muscle enhancement pad is a prosthetic format of gastrocnemius muscles of the human legs, created as a foam pad, and in a full and attractive profile that depicts ideal muscle tone. This pad can be applied directly to the calf area by hypoallergenic adhesive. In a preferred embodiment, the calf muscle enhancement pad is made of ethylene propylene diene monomer (EPDM) foam of closed-cell format in the shape of a semicircular column, and includes a profile of a gastrocnemius muscle on a convex plane. The pad measures approximately eight inches in length by five inches in width (8"×5") and has varying depth ranging from approximately one-quarter inch to three inches (¼"-3"). On an interior concave plane of each calf muscle enhancement pad is pressure-sensitive adhesive (PSA), sealed by wax paper lining until time of application upon a wearer. The pressure-sensitive adhesive is of low-residue format and its adherence properties can be reinvigorated with a light cleaning. The calf muscle enhancement pad includes a temporary, non-surgical calf enhancement member for improving an overall appearance of a leg of a user-wearer.

In certain embodiments, the calf muscle enhancement pad may include hosiery having pockets configured to receive and host the calf muscle enhancement pad. In other embodiments, hosiery may be provided with a built-in calf muscle enhancement pad. The calf muscle enhancement pad may be made in formats of filled pouches, and the pouches may be filled with various materials, including but not limited to cloth, foam, and silicone. Additionally, the calf muscle enhancement pad may be made in inflatable formats which will allow the user to determine the firmness of the calf muscle enhancement pad. In this embodiment, the pad may be inflatable by pump, mouth or other means. The calf muscle enhancement pad can be made in various sizes and shapes, and/or may be made in a single size and shape that can be personalized with modifications by a user. The calf muscle enhancement pad can be used with other corresponding clothing of applicability, such as but not limited to yoga pants and thermal underwear, in which its padding can be sewn within the garment. The calf muscle enhancement pad can be made in formats designed for attachment to prosthetic lower limbs, and to give amputees an appearance of normal leg muscle while wearing pants or full hosiery.

To use the primary embodiment of the calf muscle enhancement pad a user may simply remove the wax paper lining that covers the pressure-sensitive adhesive, and then apply the pad to a calf area. After this application, the user can engage in social and/or occupational environments with more self-confidence, and with more productivity as a result of that self-confidence.

Referring now more specifically to the drawings by numerals of reference, there is shown in FIGS. 1-5, various views of a calf muscle enhancement pad 100.

FIG. 1 shows a calf muscle enhancement pad 100 during an 'in-use' condition 150, according to an embodiment of the present disclosure. Here, the calf muscle enhancement pad 100 may be beneficial for use by a user-wearer 40 to enhance a natural appearance of a calf portion 10 of a leg of a user-wearer 40 during wear. As illustrated, the calf muscle enhancement pad 100 may include a pad 110 with a body 112 having a concave first-side 114 and a second-side 116 opposing the first-side 114. The first-side 114 includes an adhesive layer 120 for removably securing the pad 110 to a calf portion 10 of a leg of a user-wearer 40. The second-side 116 includes a calf-muscle-like extension comprising a profile of a sculpted calf muscle for enhancing a natural appearance of the calf portion 10 of the leg of the user-wearer 40 during wear.

Figure 2:
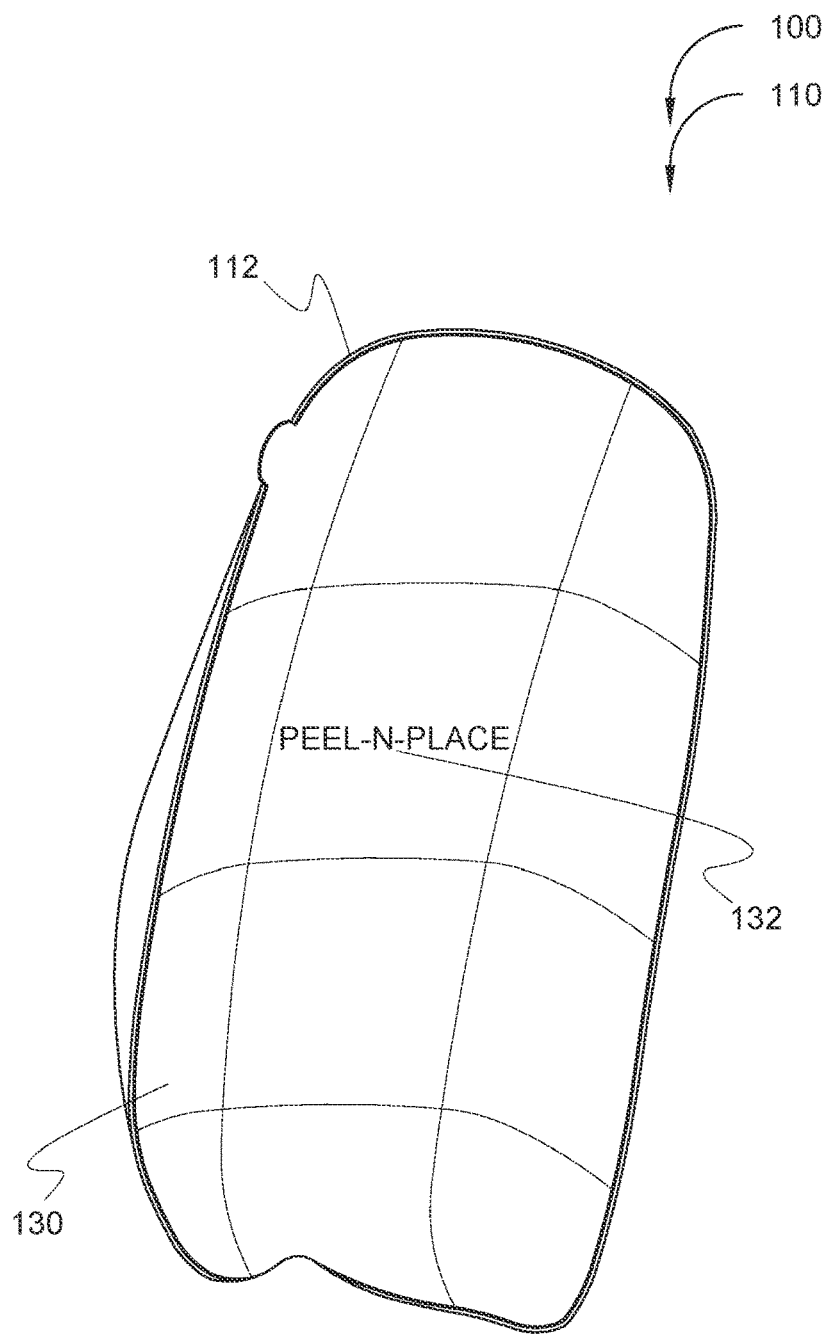
FIG. 2 is a rear view of the calf muscle enhancement pad of FIG. 1, according to an embodiment of the present disclosure.
Figure 3:
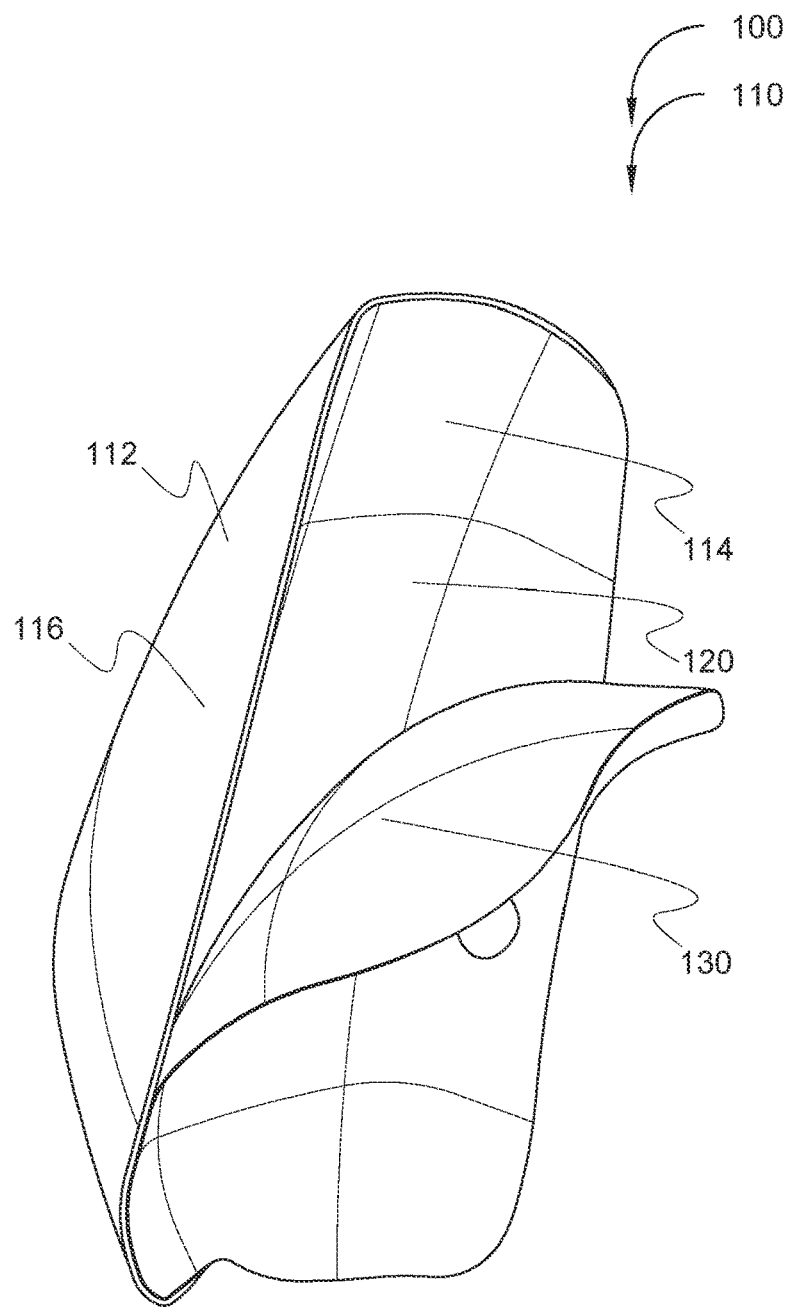
FIG. 3 is a rear view of the calf muscle enhancement pad of FIG. 1, according to an embodiment of the present disclosure.

FIGS. 2-3 show the calf muscle enhancement pad 100 of FIG. 1, according to an embodiment of the present disclosure. As above, the calf muscle enhancement pad 100 may include the pad 110 defined by the body 112 including the first-side 114 and the second-side 116 opposing the first-side 114. The pad 110 includes a semi-circular columnar profile and an ergonomic curvature 124 at a bottom-end 126. As illustrated, the first-side 114 includes an adhesive layer 120 for removably securing the pad 110 to a calf portion 10 of a leg of a user-wearer 40. The adhesive layer 120 may include a hypo-allergenic, low-residue, pressure-sensitive adhesive for temporarily adhering the pad 110 to a leg. The pad 110 further includes a removable cover 130 for concealing the adhesive layer 120 before use. In a preferred embodiment, the removable cover 130 comprises a sheet of wax paper sized and configured to cover the adhesive layer 120 before use. The removable cover 130 may include instructional indicia 132 to assist a user with removal of the removable cover 130 and application of the pad 110.

Figure 4:
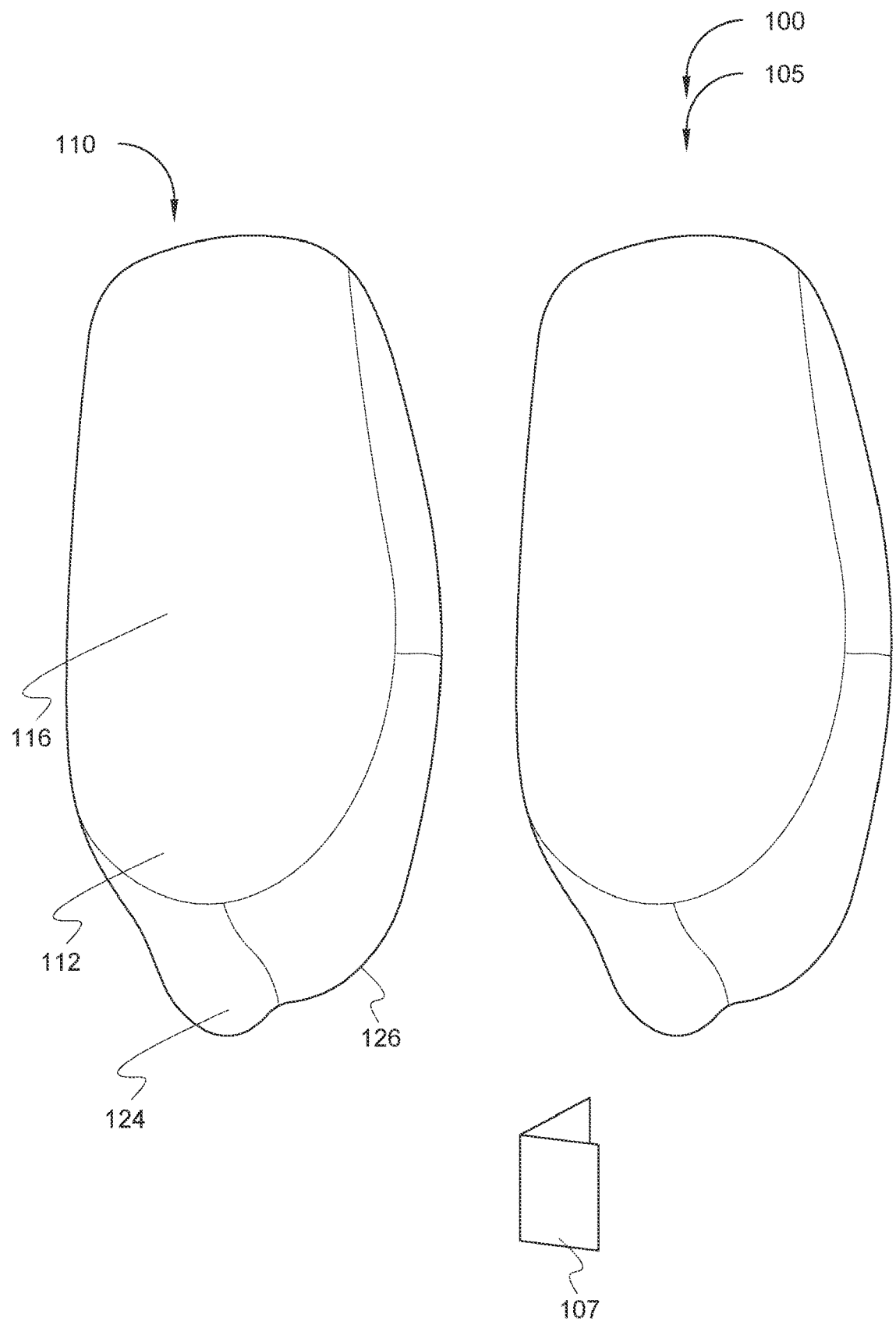
FIG. 4 is a view of a kit of the calf muscle enhancement pad of FIG. 1, according to an embodiment of the present disclosure.

FIG. 4 illustrates the calf muscle enhancement pad 100 of FIG. 1, according to an embodiment of the present disclosure. According to one embodiment, the calf muscle enhancement pad 100 may be arranged as a kit 105. In particular, the calf muscle enhancement pad 100 may further include a set of instructions 107. The instructions 107 may detail functional relationships in relation to the structure of the calf muscle enhancement pad 100 such that the calf muscle enhancement pad 100 can be used, maintained, or the like, in a preferred manner.

Figure 5:
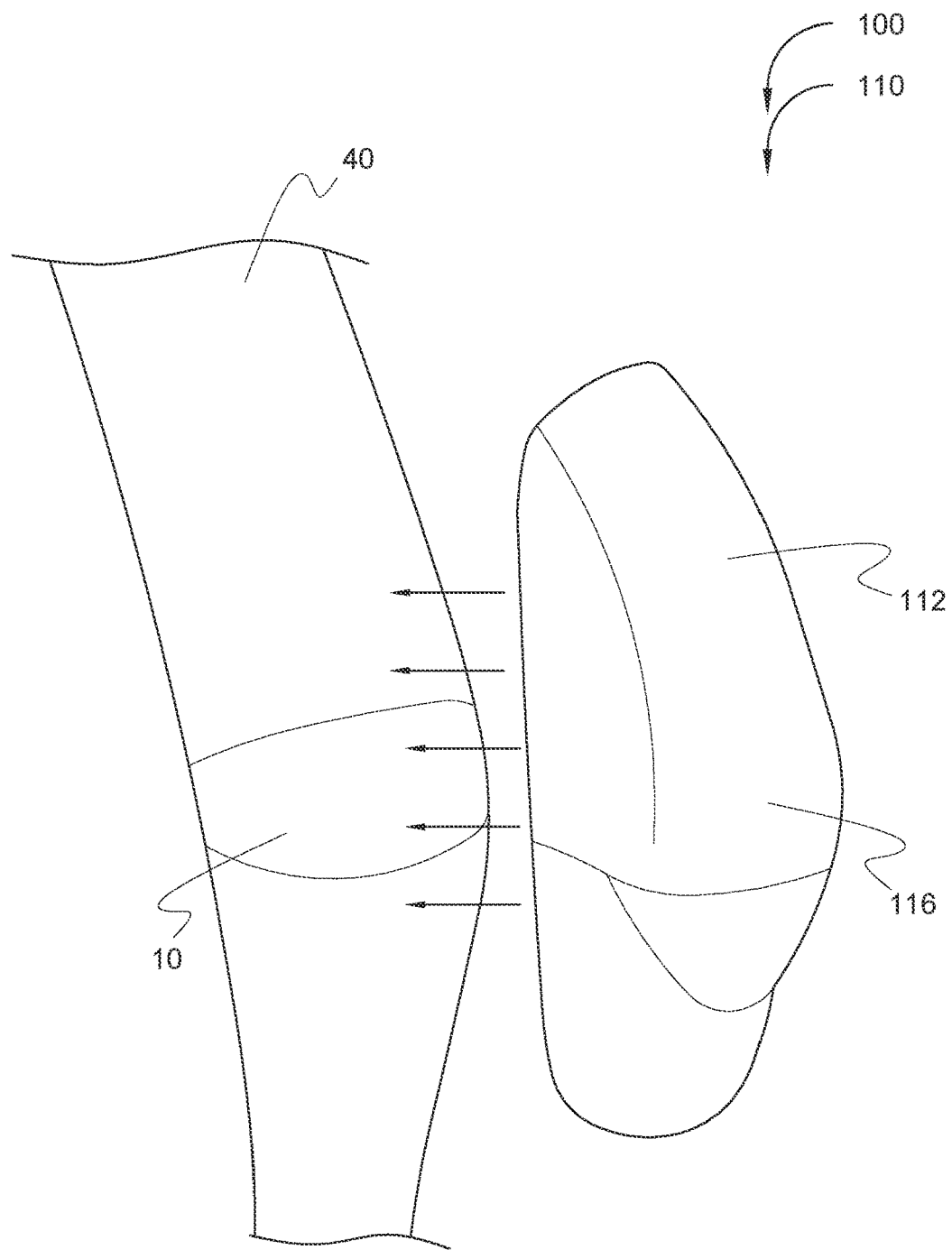
FIG. 5 is a perspective view of the calf muscle enhancement pad of FIG. 1 during a 'ready-for-use' condition, according to an embodiment of the present disclosure.

FIG. 5 is a perspective view of the calf muscle enhancement pad 100 of FIG. 1 being applied to the calf portion 10 of the leg of the user-wearer 40, according to an embodiment of the present disclosure. The pad 110 is flexible and is configured to contour to the calf portion 10 of the leg of the user-wearer 40 during wear. In a preferred embodiment, the pad 110 comprises a length of approximately 8 inches and a width of approximately 5 inches. The pad 110 may comprise a minimum depth of approximately 0.25 inch and a maximum depth of approximately 3 inches. The pad 110 comprises a foam material. The calf muscle enhancement pad 110 may be made of various materials of applicability, such as but not limited to ethylene propylene diene monomer (EPDM) foam, polyurethane (PU) foam, compressed polyester, and polyester fiberfill. In foam formats, the foam may be open-cell or closed-cell. The calf muscle enhancement pad 110 provides an appearance of a fully-developed, muscular, and toned calf muscle.

In certain embodiments, the pad 110 of the calf muscle enhancement pad 100 is provided with hosiery such as but not limited to stockings, panty hose, socks, and pants. The hosiery may be used in conjunction with the pad 110. The hosiery may include pockets configured to receive and host one of the pads 110. The pad 110 may be removable from the hosiery or may be integral to the hosiery and non-removable from the hosiery.

Figure 6:
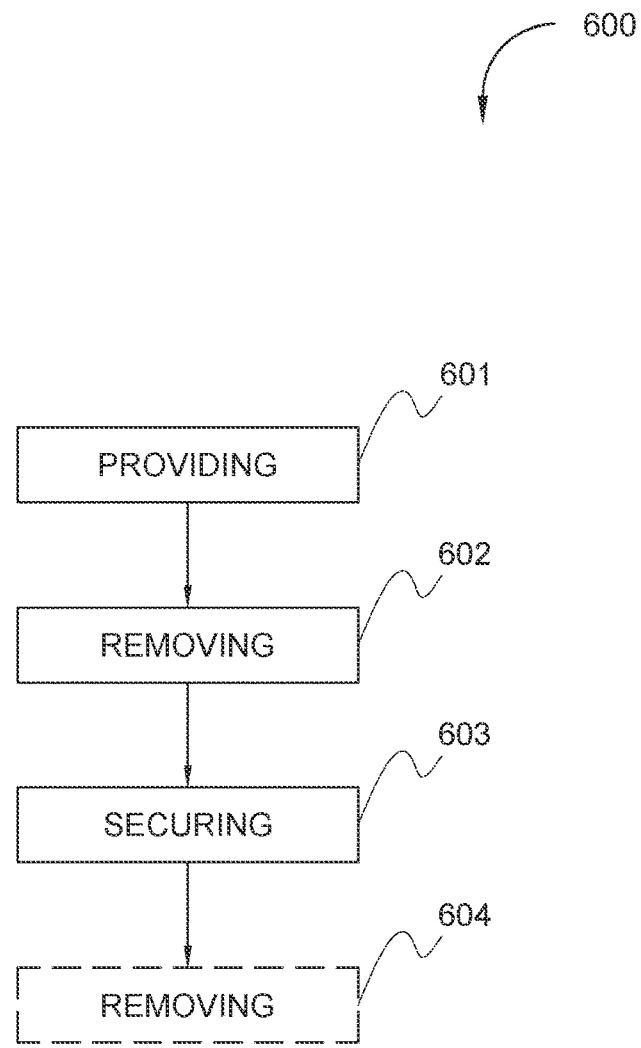
FIG. 6 is a flow diagram illustrating a method of using the calf muscle enhancement pad to enhance a natural appearance of a calf portion of a leg, according to an embodiment of the present disclosure.

FIG. 6 is a flow diagram illustrating a method of using the calf muscle enhancement pad 100 to enhance a natural appearance of a calf portion of a leg, according to an embodiment of the present disclosure. In particular, the method for using the calf muscle enhancement pad to enhance a natural appearance of a calf portion of a leg 600 may include one or more components or features of the calf muscle enhancement pad 100 as described above. As illustrated, the method for using the calf muscle enhancement pad 600 may include the steps of: step one 601, providing a pad 110 with a body 112 having a concave first-side 114 including an adhesive layer 120 for removably securing the pad 110 to a calf portion 10 of a leg of a user-wearer 40 and a second-side 116 opposing the first-side 114 and having a calf-muscle-like extension comprising a profile of a sculpted calf muscle for enhancing a natural appearance of the calf portion 10 of the leg of the user-wearer 40 during wear; step two 602, removing a removable cover 130 and exposing the adhesive layer 120 of the concave first-side 114 of the pad 110; step three 603, securing the pad 110 to the calf portion 10 of the leg of the user-wearer 40; and step four 604, removing the pad 110.

It should be noted that step four 604 is an optional step and may not be implemented in all cases. Optional steps of method of use 600 are illustrated using dotted lines in FIG. 6 so as to distinguish them from the other steps of method of use 600. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for using the calf muscle enhancement pad 100, are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A calf muscle enhancement pad, said calf muscle enhancement pad comprising:
   a pad with a body having,
   a concave first-side including an adhesive layer for removably securing said pad to a calf portion of a leg of a user-wearer, and
   a second-side opposing said first-side and having a calf-muscle-like extension comprising a profile of a sculpted calf muscle for enhancing a natural appearance of said calf portion of said leg of said user-wearer during wear, the sculpted profile defined by three distinct sections including a first section, a second section, and a third section, where each of the first section, second section, and third section are disposed at an angle relative to an adjacent section, and
   wherein said pad further includes a removable cover for concealing said adhesive layer before use;
   wherein said removable cover comprises a sheet of wax paper sized and configured to cover said adhesive layer before use;
   wherein said removable cover comprises instructional indicia;
   wherein said adhesive layer comprises a pressure-sensitive adhesive;
   wherein said pad comprises an ethylene propylene diene monomer foam material;
   wherein said pad is flexible and is configured to contour to said calf portion of said leg of said user-wearer during wear;
   wherein said pad comprises an ergonomic curvature at a bottom-end;
   wherein said pad comprises a semi-circular columnar profile; and
   wherein the pad has a length of 8 inches and a width of 5 inches, and a minimum depth of 0.25 inch and a maximum depth of 3 inches.

2. A calf muscle enhancement pad, said calf muscle enhancement pad consisting of:
   a pad with a body having,
   a concave first-side including an adhesive layer for removably securing said pad to a calf portion of a leg of a user-wearer, and
   a second-side opposing said first-side and having a calf-muscle-like extension comprising a profile of a sculpted calf muscle for enhancing a natural appearance of said calf portion of said leg of said user-wearer during wear, the sculpted profile defined by a first section, a second section, and a third section, where each of the sections are disposed at an angle relative to an adjacent section, and
   wherein said pad further includes a removable cover for concealing said adhesive layer before use;
   wherein said removable cover comprises a sheet of wax paper sized and configured to cover said adhesive layer before use;
   wherein said removable cover comprises instructional indicia;
   wherein said adhesive layer comprises a pressure-sensitive adhesive;
   wherein said pad comprises an ethylene propylene diene monomer foam material;
   wherein said pad is flexible and is configured to contour to said calf portion of said leg of said user-wearer during wear;
   wherein said pad comprises an ergonomic curvature at a bottom-end;
   wherein said pad comprises a semi-circular columnar profile; and
   wherein the pad has a length of 8 inches and a width of 5 inches, and a minimum depth of 0.25 inch and a maximum depth of 3 inches.

* * * * *